(12) United States Patent
Genis (10) Patent No.: US 8,976,343 B2
(45) Date of Patent: Mar. 10, 2015

(54) LASER CRYSTAL DEGRADATION COMPENSATION

(71) Applicant: KLA-Tencor Corporation, Milpitas, CA (US)

(72) Inventor: Patrick C. Genis, Boulder Creek, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 100 days.

(21) Appl. No.: 13/905,346

(22) Filed: May 30, 2013

(65) Prior Publication Data

US 2013/0342832 A1    Dec. 26, 2013

Related U.S. Application Data

(60) Provisional application No. 61/662,484, filed on Jun. 21, 2012.

(51) Int. Cl.
  *G01N 21/00*  (2006.01)
  *G01N 21/88*  (2006.01)
  *G02F 1/35*   (2006.01)

(52) U.S. Cl.
  CPC ......... *G01N 21/8806* (2013.01); *G02F 1/3525* (2013.01)
  USPC .......................................................... 356/30

(58) Field of Classification Search
  USPC .................................. 356/30, 237.1
  See application file for complete search history.

(56) References Cited

U.S. PATENT DOCUMENTS

| | | | |
|---|---|---|---|
| 4,178,561 A | 12/1979 | Hon et al. | |
| 5,520,679 A * | 5/1996 | Lin | 606/5 |
| 5,825,562 A | 10/1998 | Lai et al. | |
| 6,388,534 B1 | 5/2002 | Balzano et al. | |
| 6,859,335 B1 | 2/2005 | Lai et al. | |
| 6,890,474 B2 | 5/2005 | Gruber et al. | |
| 2006/0072635 A1 | 4/2006 | Wang | |
| 2008/0144678 A1 | 6/2008 | Lu | |
| 2010/0111119 A1 | 5/2010 | Sato et al. | |
| 2011/0222565 A1 | 9/2011 | Horain et al. | |
| 2012/0033291 A1 | 2/2012 | Kneip | |
| 2012/0113995 A1 | 5/2012 | Armstrong | |

FOREIGN PATENT DOCUMENTS

EP    1194804 A2    12/2000

* cited by examiner

*Primary Examiner* — Abdullahi Nur
(74) *Attorney, Agent, or Firm* — Suiter Swantz pc llo (57) ABSTRACT

Method and system for laser crystal degradation compensation are disclosed. The method includes: defining a plurality of sites on a frequency converting crystal; determining a degradation rate associated with each of the plurality of sites; determining an amount of time T wherein a site is continuously operable within a tolerated variation of at least one beam parameter, the amount of time T being determined based on the tolerated variation of the at least one beam parameter and the degradation rate; determining an amount of time t wherein t is a fraction of T; and iteratively shifting among the plurality of sites, wherein each of the plurality of sites is utilized continuously for a duration of time t for each iteration.

20 Claims, 8 Drawing Sheets

LASER CRYSTAL DEGRADATION COMPENSATION

CROSS-REFERENCE TO RELATED APPLICATIONS

The present application claims the benefit under 35 U.S.C. §119(e) of U.S. Provisional Application Ser. No. 61/662,484, filed Jun. 21, 2012. Said U.S. Provisional Application Ser. No. 61/662,484 is hereby incorporated by reference in its entirety.

TECHNICAL FIELD

The disclosure generally relates to the field of inspection systems, and particularly to a laser source for inspection systems.

BACKGROUND

Thin polished plates such as silicon wafers and the like are a very important part of modern technology. A wafer, for instance, may refer to a thin slice of semiconductor material used in the fabrication of integrated circuits and other devices. Other examples of thin polished plates may include magnetic disc substrates, gauge blocks and the like. While the technique described here refers mainly to wafers, it is to be understood that the technique also is applicable to other types of polished plates as well. The term wafer and the term thin polished plate may be used interchangeably in the present disclosure.

Semiconductor materials may be inspected for defects such as, e.g., surface imperfections, particles, irregularities, the thickness of thin film coatings, and the like, which may hamper the performance of the semiconductor material. Some existing inspection systems direct a beam of radiation on the surface of the semiconductor material, then collect and analyze light reflected and/or scattered from the surface to quantify characteristics of the surface.

More specifically, existing systems generally utilize a beam scanner created by having a laser source focused on a crystal. The crystal is shifted to a fresh area when the currently exposed area has degraded to an undesirable level (i.e., end of life). While shifting from a discrete crystal site at the end of its life is appropriate for the defined limits on lifetime of a laser sub-system, however, from a system perspective, shifting from an exposed area that has degraded to its end of life to a fresh area requires re-calibration or re-alignment, which is very time consuming.

Therein lies a need for providing a laser source for inspection systems without the aforementioned shortcomings.

SUMMARY

The present disclosure is directed to a method for laser crystal degradation compensation. The method includes: defining a plurality of sites on a frequency converting crystal; determining a degradation rate associated with each of the plurality of sites; determining an amount of time T wherein a site is continuously operable within a tolerated variation of at least one beam parameter, the amount of time T being determined based on the tolerated variation of the at least one beam parameter and the degradation rate; determining an amount of time t wherein t is a fraction of T; and iteratively shifting among the plurality of sites, wherein each of the plurality of sites is utilized continuously for a duration of time t for each iteration.

A further embodiment of the present disclosure is also directed to a method for laser crystal degradation compensation. The method includes: defining a plurality of sites on a frequency converting crystal; determining an initial operating condition associated with each of the plurality of sites; establishing a ranking order based on the initial operating condition associated with each of the plurality of sites; determining a degradation rate associated with each of the plurality of sites; determining an amount of time T wherein a site is continuously operable within a tolerated variation of at least one beam parameter, the amount of time T being determined based on the tolerated variation of the at least one beam parameter and the degradation rate; determining an amount of time t wherein t is a fraction of T; and iteratively shifting among the plurality of sites according to the established ranking order, wherein each of the plurality of sites is utilized continuously for a duration of time t for each iteration.

An additional embodiment of the present disclosure is directed to an illumination apparatus. The illumination apparatus includes a laser source and a crystal. The crystal is configured for receiving a laser from the laser source and providing a frequency converted beam as output. The crystal includes a plurality of sites defined thereof, wherein each particular site of the plurality of sites is associated with: a degradation rate, and an amount of time T wherein that particular site is continuously operable within a tolerated variation of at least one beam parameter, and wherein the crystal is iteratively shifted among the plurality of sites such that each of the plurality of sites is utilized continuously for a duration of time t for each iteration wherein t is a fraction of T.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

Figure 1:
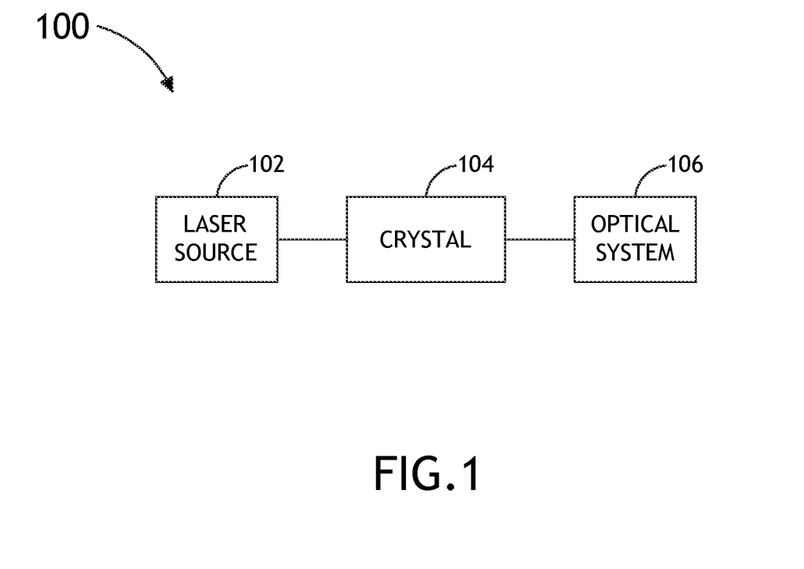
FIG. 1 is a block diagram depicting an illumination system.

Referring to FIG. 1, a block diagram depicting an exemplary illumination system 100 is shown. The illumination system 100 includes a laser source 102 configured for delivering a laser to a frequency converting crystal 104. The crystal 104 in turn produces a beam of a particular wavelength (e.g., ultraviolet or deep ultraviolet output) to provide illumination for an optical/inspection system 106. It is contemplated that the crystal 104 is configured to shift positions in order to extend its lifetime.

Figure 2:
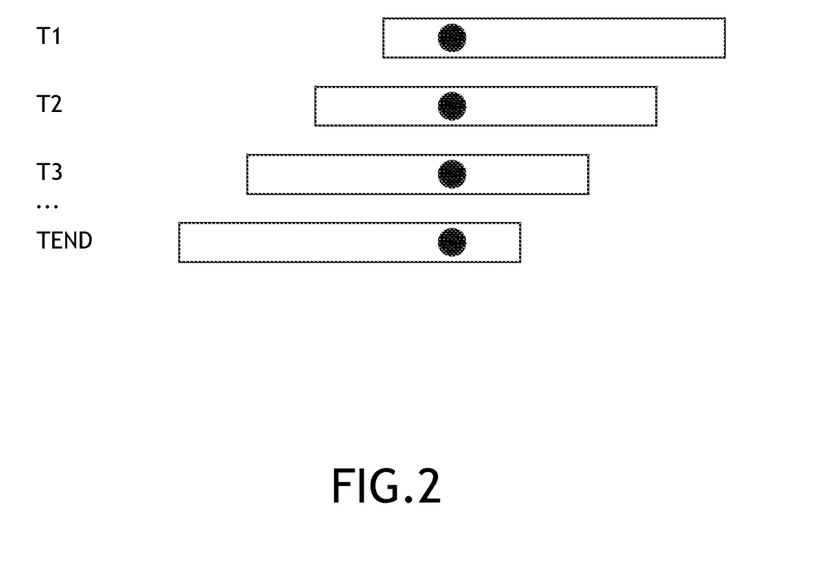
FIG. 2 is a series of cross-sectional views depicting shifting of a frequency conversion crystal over time.

FIG. 2 is a series of cross-sectional views depicting the shifting of the crystal sites (may also be referred to as areas or spots) for receiving the laser beam over time. A shifting mechanism may be utilized to shift the relative positions of the laser source 102 and the crystal 104. This shifting operation may continue till $T_{end}$, when shifting may repeat again from the position shown in $T_1$, or when the crystal 104 may have reached the full lifetime and need to be replaced.

Figure 3:
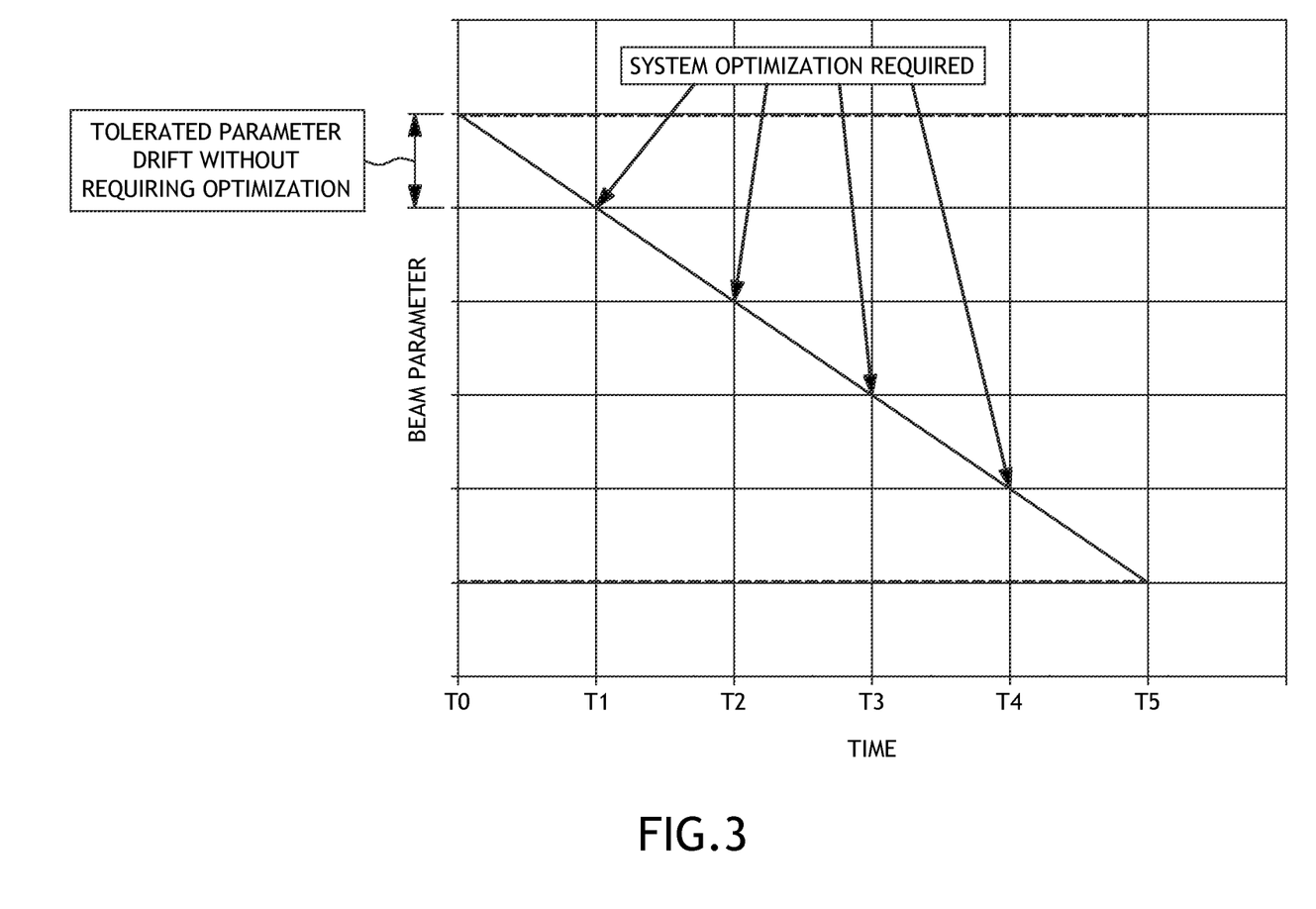
FIG. 3 is an illustration depicting degradation of a beam parameter.

It is noted that each given crystal site degrades over time when it is utilized. More specifically, the parameters (e.g., waist location, waist diameter, astigmatism, beam shape, power, noise, M-squared, or the like) associated with the output beam produced by a given crystal site degrades over time. FIG. 3 shows a simplified illustration depicting degradation of a crystal site when it is used continuously. For illustrative purposes, suppose the beam parameters observed at time T1 degrade to a level too far apart from the initial level observed at T0, the optical system may need to be optimized in order to compensate for the degradation. Furthermore, this degradation may continue to the point when the end of life of that particular crystal site is reached and the crystal needs to be shifted to a new site. Since the beam parameters of an end-of-life site greatly differ from that of a new site, a major system re-calibration or re-alignment is generally required. It is noted that system optimization and re-calibration processes are time consuming and need to be avoided when possible.

The present disclosure is directed to systems and methods to mitigate the adverse effects on the optical system due to laser beam parameter drifts. In accordance with the present disclosure, the crystal is recursively/iteratively shifted at appropriate intervals and in particular manners in order to reduce the number of system optimization and/or re-calibration processes needed.

More specifically, in one embodiment, each given crystal site in the crystal 104 is pre-characterized to determine its initial operating condition and whether the beam parameters produced at each particular crystal site is within a specific illumination requirement. Additionally, representative degradation rates for the crystal sites can be pre-determined based on analysis of similar or substantially identical crystals. For instance, degradation of a particular crystal site may be observed over time, which may be used as the representative degradation rate for the same type of crystals in subsequent uses. Alternatively, a set of crystal sites selected from one or more different crystals may be observed over time and an overall average may be obtained. It is contemplated that various other statistical and/or analysis techniques may be utilized to obtain such representative degradation rates for crystal sites without departing from the spirit and scope of the present disclosure.

Figure 4:
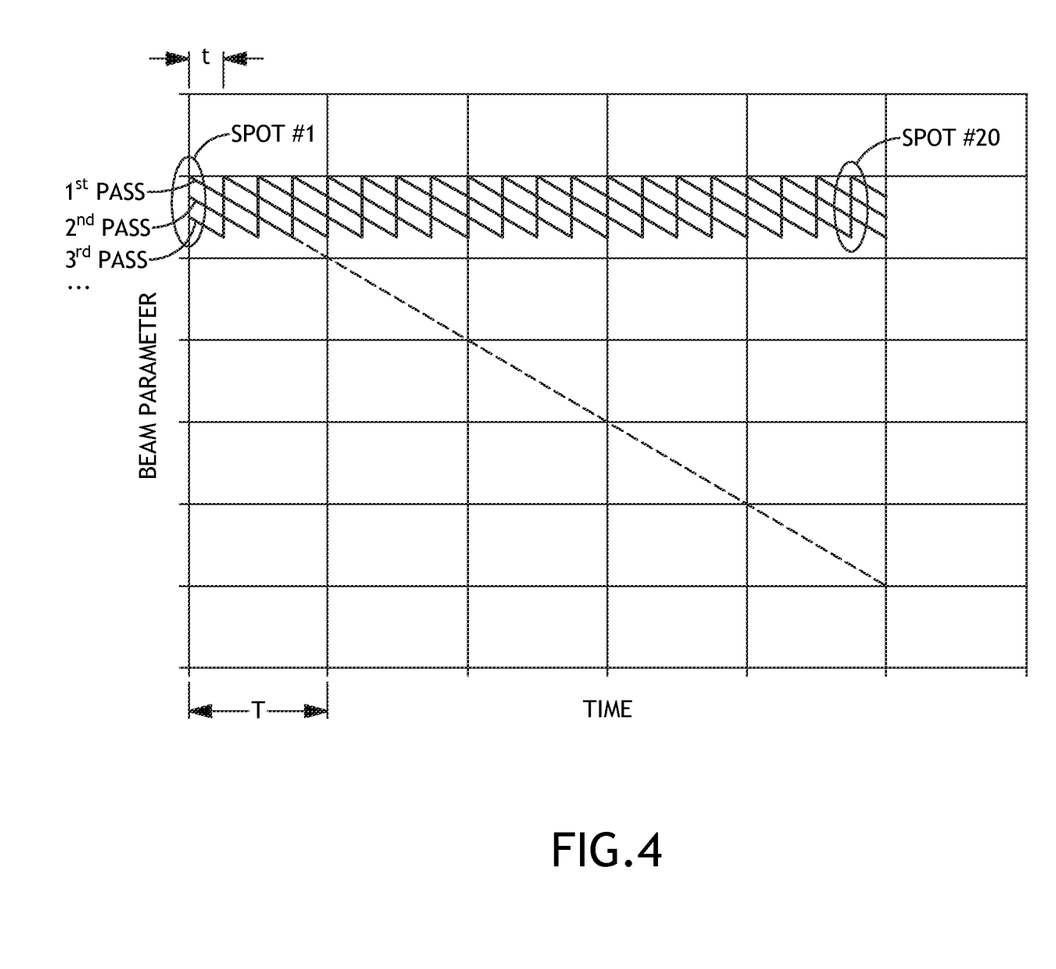
FIG. 4 is an illustration depicting degradation of a beam parameter when a crystal is iteratively shifted in accordance with an embodiment of the present disclosure.

Referring now to FIG. 4, a simplified illustration depicting degradations of recursively shifted crystal sites in accordance with one embodiment of the present disclosure is shown. In the example depicted in FIG. 4, the crystal being utilized has 20 discrete sites/spots that have the same initial beam parameters and the same degradation rate. As depicted in FIG. 4, each of the 20 sites is utilized only for a short interval t and is shifted to the next one. A complete pass (i.e., iteration) is performed when each of the 20 sites is access once and only once, and this shifting process repeats recursively as illustrated in the figure.

More specifically, as shown in FIG. 3 when each crystal site is used continuously till its end-of-life and then subsequently shifted to the next site, five optimizations are required (e.g., at T1 through T5) per site. In comparison, when the crystal sites are recursively shifted as shown in FIG. 4, each site is utilized only for a short interval t during a given iteration, and system optimization is only required after four iterations in the example shown in FIG. 4 (i.e., when all 20 sites degrade to a lower level). Recursively shifting the crystal after a short interval t in accordance with the present disclosure effectively reduces the number of system optimizations required by a factor of 20 in this example. Additionally, a major re-calibration or re-alignment is not required as was for a single site continuous approach. That is, while a major system re-calibration or re-alignment is generally required when shifting from an end-of-life site to a fresh site, however, in accordance with this embodiment of the present disclosure, the crystal is shifted from one site to another only after a short interval t, and the crystal is never shifted from an end-of-life site to a fresh site. Therefore, the differences in beam parameters introduced as the result of such a shift are significantly reduced and no major system re-calibration or re-alignment is required. It is contemplated that when the final pass is completed, which would be 20 passes for the example shown in FIG. 4, all sites would be equally out-of-specification with respect to the system requirement and the entire crystal can be replaced.

It is contemplated that the interval t referenced in the example above is a fraction of the time interval T (e.g., t=T/n). As described above, the time interval T indicates when the beam parameters have degraded to a level beyond the tolerable amount of beam parameter drifts, in which case the system need to be optimized in order to compensate for the degradation. It is understood that the amount of parameter drifts tolerated by a particular optical/inspection system may vary based on the specific requirements, and therefore the time interval T may vary accordingly. It is also contemplated that while t=T/4 in the example above, T is not required to be divisible by t. The interval t may be any duration as long as it is less than the time interval T without departing from the spirit and scope of the present disclosure.

It is also contemplated that the crystal sites are not required to be pre-characterized in order to implement the techniques described above. That is, each site can be characterized on-the-fly the first time that particular site is utilized. Such an on-the-fly characterization process may reduce the setup time required when a new crystal is used.

Figure 5:
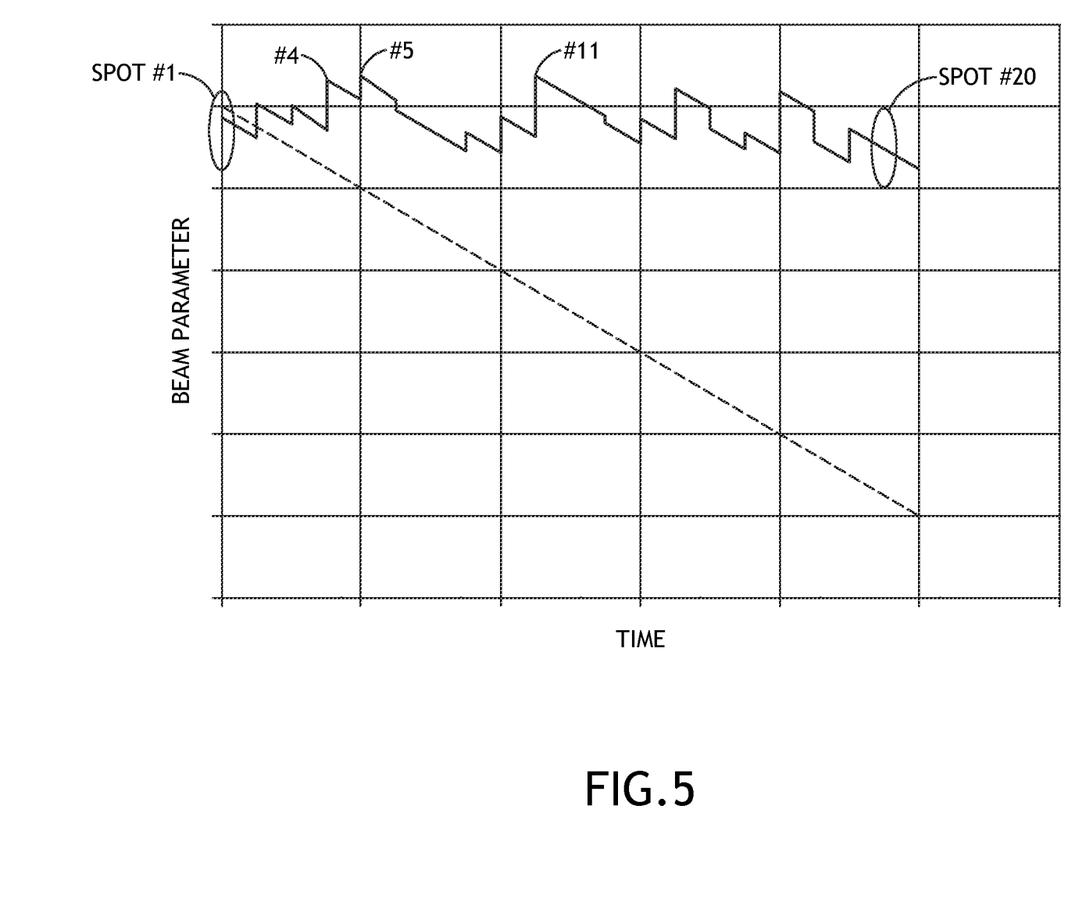
FIG. 5 is an illustration depicting degradation of a beam parameter when a crystal having crystal sites with non-uniform initial conditions is iteratively shifted.

It is further contemplated that the initial conditions of different sites/spots within the same crystal may vary slightly. For instance, the initial beam parameters observed at some crystal sites may differ from that observed at some other sites even within the same crystal. When such a crystal is used in the illumination system, sequentially shifting from crystal sites located on one end of the crystal to the other may produce some undesirable results. FIG. 5 shows a simplified illustration depicting the differences in beam parameters if the initial conditions of the different sites within the same crystal are different and if the crystal is shifted sequentially from one end to another. In some instances, there can be large discontinuities in beam parameters that may exceed the system's tolerance for change without a required optimization.

To mitigate the adverse effects of such differences associated with different sites, in accordance with certain embodiments of the present disclosure, the crystal is shifted in an ordered manner based on a pre-determined ranking of the crystal sites. More specifically, the crystal sites within the same crystal are ranked according to one or more beam parameters. Once a ranking is established, the crystal is shifted according to the ranking order (as opposed to simply from one end to the other) to reduce/mitigate abrupt changes.

Figure 6:
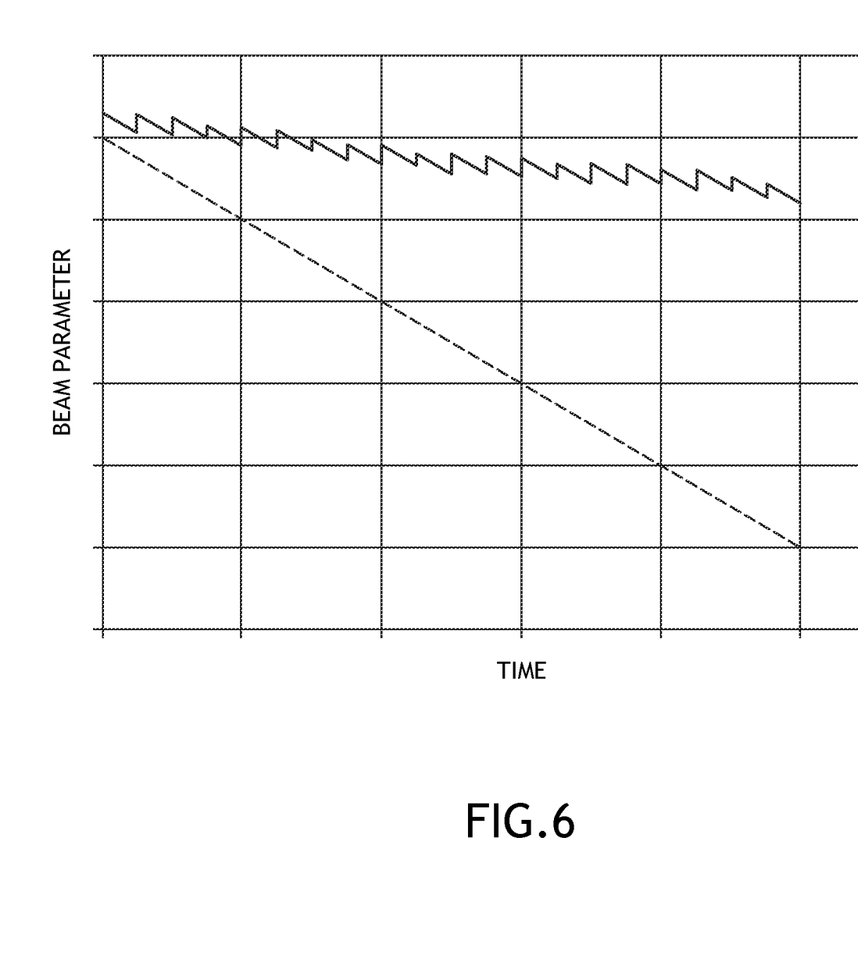
FIG. 6 is an illustration depicting degradation of a beam parameter when the crystal of FIG. 5 is iteratively shifted according to an established order.

FIG. 6 is an illustration depicting the same crystal as shown in FIG. 5 shifted according to the established ranking order instead. In this example, the different sites are ranked in a descending order based on the observed beam parameters. More specifically, suppose that the crystal sites are indexed from left to right as site #1 through site #20, and suppose that the observed beam parameters associated with site #11 have the highest value, followed by site #5, site #4 and so on (as shown in FIG. 5). Based on this ranking, site #11 (the highest ranking site) may be used first for a time period t, then shifted to site #5 (the second highest ranking site), followed by site #4 and so on to complete the first pass. Subsequent passes will be performed in the same ranking order and therefore have a similar curve offset down by one degradation increment. In this manner, the crystal is shifted to provide less abrupt changes.

It is contemplated that the established ranking order is not limited to a descending order as illustrated in the example above. For instance, some beam parameters may increase when they degrade, and in such cases, the different sites may be ranked in an ascending order without departing from the spirit and scope of the present disclosure. It is also contemplated that ranking may be extended to variable intervals based on expected degradation rates or the initial beam parameter values.

Furthermore, in an alternative embodiment, sites producing similar beam parameters may be arrange into bins/groups. For example, the 20 crystal sites shown in the figures may be grouped into two groups of 10 each or 5 groups of 4 each. One particular group may be recursively accessed until that particular group hits end-of-life whereupon the next group may then be accessed and the process continues. It is contemplated, however, that the groups are not required to be identical in size.

In another alternative embodiment, only the crystal sites in the highest ranking group may be accessed recursively until their beam parameters have degraded to substantially the same level as the next highest group. The crystal sites in these two groups can then operate together as one merged group until their beam parameters have degraded to substantially the same level as the next group, at which point they may merge again to form an even larger group. This process may continued until the condition is reached where all sites are merged into a single group, in which case all crystal sites now have substantially similar beam parameters and the same technique described in FIG. 4 can be utilized.

Figure 7:
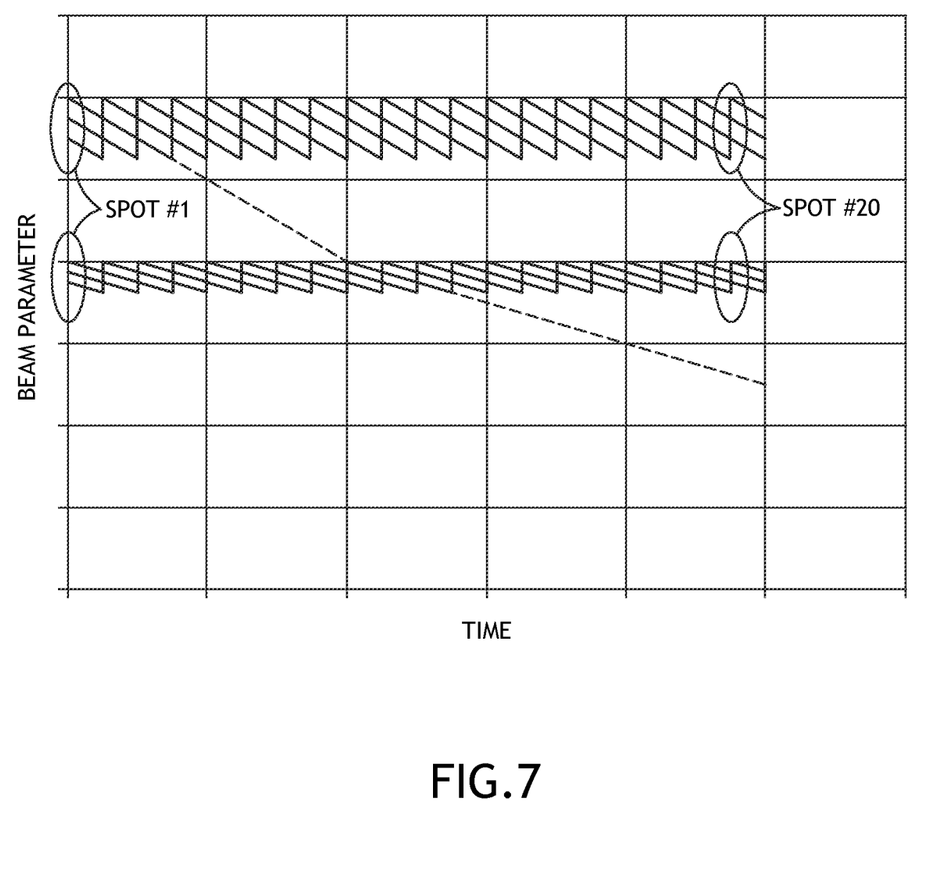
FIG. 7 is an illustration depicting iteratively shifting of a crystal having non-linear degradation.
Figure 8:
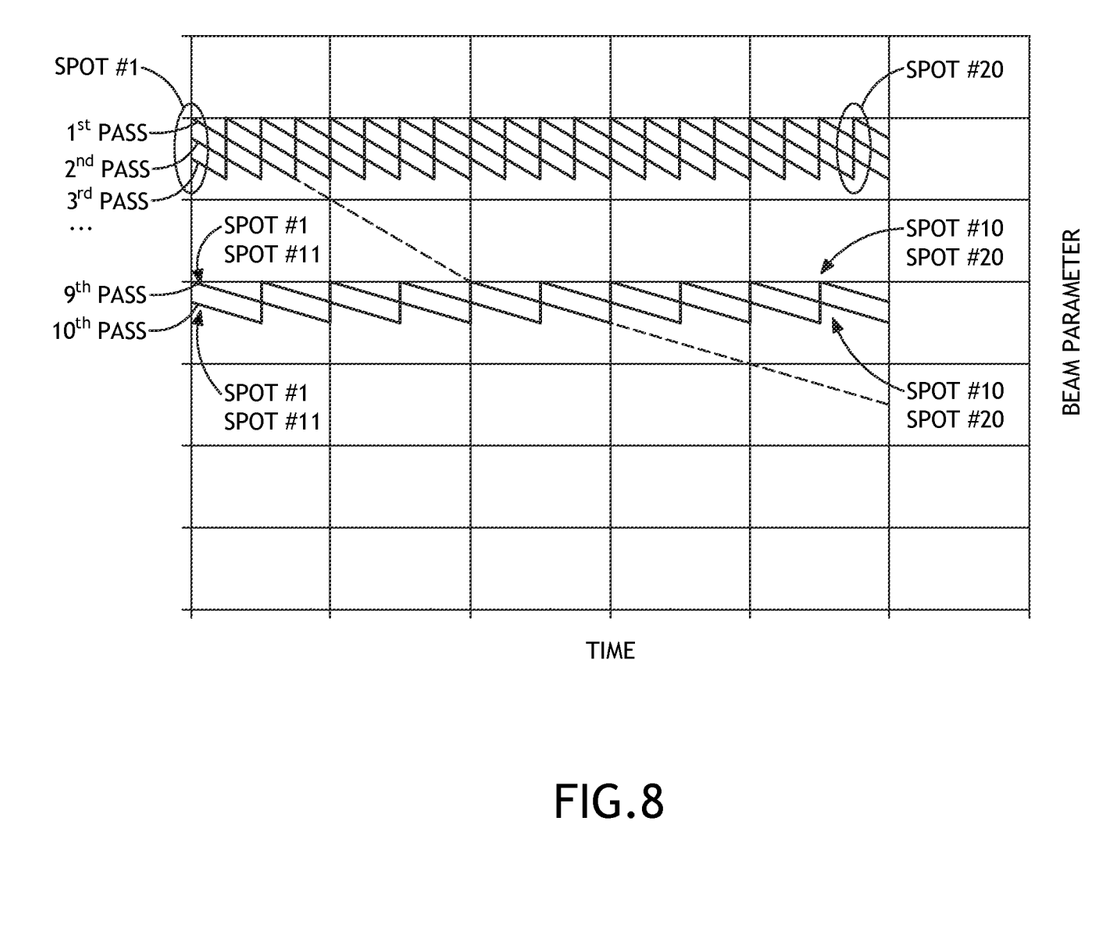
FIG. 8 is an illustration depicting an alternative iteratively shifting of the crystal having non-linear degradation.

It is also contemplated that the methods in accordance with the present disclosure is applicable even if the crystal sites degrade in a non-linear manner. For instance, as illustrated in FIG. 7, the degradation curve may be sub-divided into several regions of relatively constant linear degradation. In this example, even though the rate of degradation slows to a half of the previous rate after the $8^{th}$ pass, the interval between site shifts (i.e., t) may be kept the same. As a result, the number of passes that can be performed without needing to optimize the system may double after the $8^{th}$ pass. Alternatively, the interval between site shifts (i.e., t) can also be adjusted relative to the change in slope as shown in FIG. 8, where one pass of the crystal may take, for example, twice as long. In both cases, the decreased rate of degradation would require less optimization efforts and thereby increase system utilization.

As illustrated in the examples above, the methods in accordance with the present disclosure provide a more uniform system performance in spite of the degradation rate of the laser. System utilization is maximized by substantially reducing the number of system optimizations needed and removing major re-alignment requirements caused by end-of-life spot shifts.

It is contemplated that the beam parameters referenced in the present disclosure may include, but not limited to, waist location, waist diameter, astigmatism, beam shape, power, noise, M-squared and the like. It is also contemplated that any one or a combination of more than one of such parameters may be used to evaluate or rank a crystal site/spot as previously described. It is contemplated that the selection of specific parameters and the weight assigned to each parameter (e.g., if a weighted average is used) may be determined based on system requirements and may vary without departing from the spirit and scope of the present disclosure.

Furthermore, it is contemplated that the crystal sites are not required to be completely spaced apart. That is, overlaps between the sites may be allowed without departing from the spirit and scope of the present disclosure.

Figure 9:
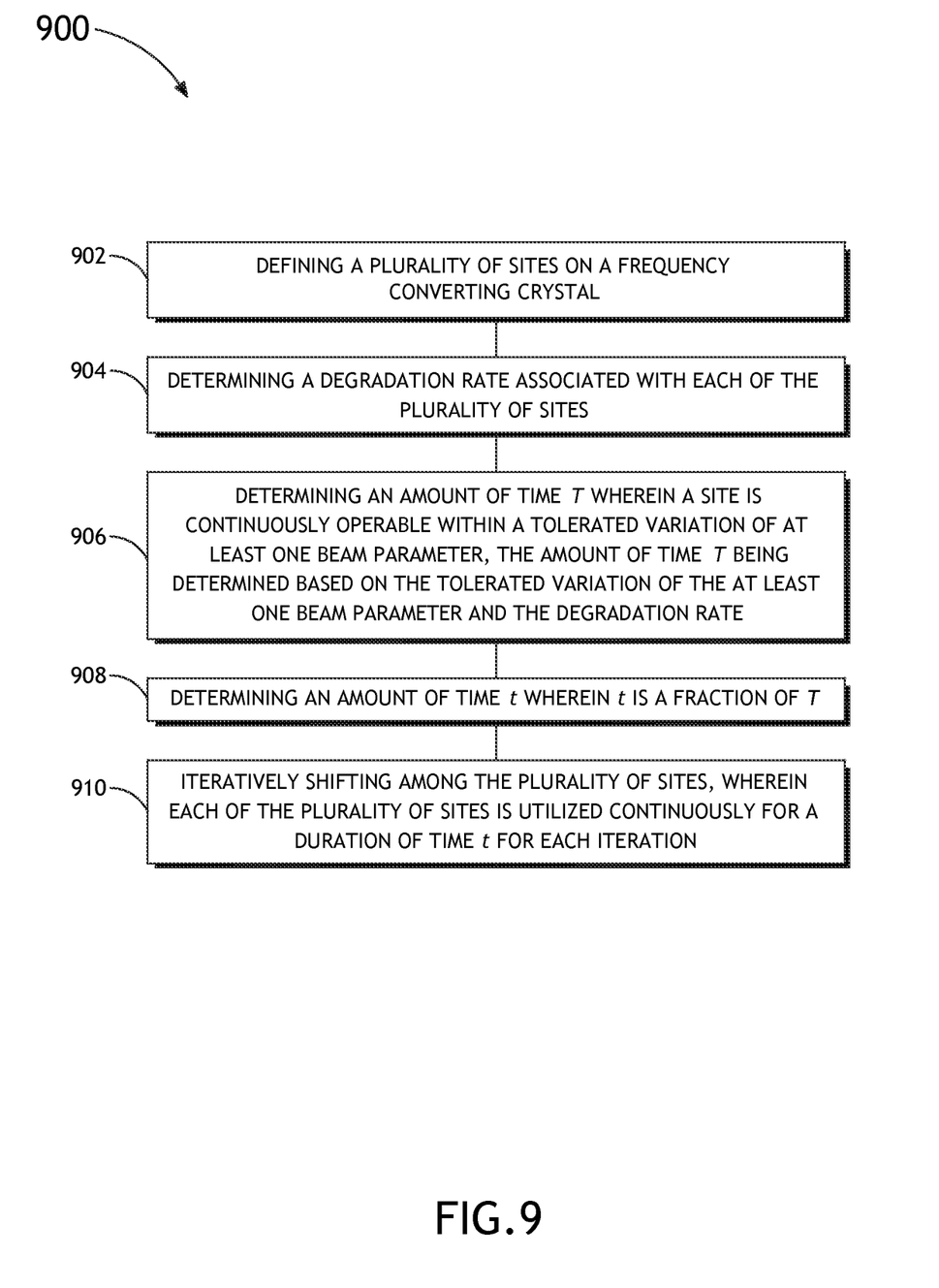
FIG. 9 is a flow diagram illustrating a method for laser crystal degradation compensation in accordance with one embodiment of the present disclosure.

FIG. 9 is a flow diagram illustrating a method 900 for laser crystal degradation compensation in accordance with the present disclosure. In one embodiment, a plurality of sites/spots may be defined on a frequency converting crystal in step 902. Step 904 may determine a degradation rate associated with each site. It is contemplated that the degradation rate may be pre-determined based on observation of one or more substantially identical crystals. Based on the degradation rate, step 906 may determine an amount of time (denoted as T) wherein a site is continuously operable within a tolerated variation of at least one beam parameter. That is, while beam parameters such as waist size, alignment variations and the like can be tolerated within a certain threshold, if the same site is continuously utilized, its associated beam parameters may degrade to a level outside of the tolerated amount which may prompt the system to perform an optimization to compensate such degradation. Therefore, the value of T represents the amount of time a site can be continuously operated without prompting a required optimization.

Step 908 may then determine the amount of time t as previously described, and step 910 may iteratively shift among the plurality of sites based on the determined t value. That is, each site should be utilized continuously for only the duration of time t for each iteration.

It is contemplated that a ranking order may also be established as described above. In one embodiment, a ranking order is established for each site, and the crystal is shifted from one site to another based on the established order. In an alternative embodiment, the various sites are arranged into multiple groups. Only the crystal sites in the highest ranking group may be accessed recursively until their beam parameters have degraded to substantially the same level as the next highest group, in which case they can be merged to form a larger group. This process may continued until the condition is reached where all sites are merged into a single group, in which case all crystal sites now have substantially similar beam parameters and the same technique described above can be utilized.

The methods disclosed may be implemented as sets of instructions, through a single production device, and/or through multiple production devices. Further, it is understood that the specific order or hierarchy of steps in the methods disclosed are examples of exemplary approaches. Based upon design preferences, it is understood that the specific order or hierarchy of steps in the method can be rearranged while remaining within the scope and spirit of the disclosure. The accompanying method claims present elements of the various steps in a sample order, and are not necessarily meant to be limited to the specific order or hierarchy presented.

It is believed that the system and method of the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory.

What is claimed is:

1. A method for laser crystal degradation compensation, comprising:
    defining a plurality of sites on a frequency converting crystal;
    determining a degradation rate associated with each of the plurality of sites;
    determining an amount of time T wherein a site is continuously operable within a tolerated variation of at least one beam parameter, the amount of time T being determined based on the tolerated variation of the at least one beam parameter and the degradation rate;
    determining an amount of time t wherein t is a fraction of T; and
    iteratively shifting among the plurality of sites, wherein each of the plurality of sites is utilized continuously for a duration of time t for each iteration.

2. The method of claim 1, wherein T represents the amount of time a site is continuously operable without prompting a required optimization to compensate for degradation.

3. The method of claim 1, wherein the same degradation rate is utilized for each of the plurality of sites.

4. The method of claim 3, wherein the degradation rate is pre-determined based on observation of at least one substantially identical crystal.

5. The method of claim 1, further comprising:
    determining an initial operating condition associated with each of the plurality of sites; and
    establishing a ranking order for iteratively shifting the plurality of sites.

6. The method of claim 5, wherein the ranking order is established based on the initial operating condition associated with each of the plurality of sites in one of: a descending order or an ascending order.

7. The method of claim 1, further comprising:
    determining an initial operating condition associated with each of the plurality of sites;
    establishing a plurality of groups based on the initial operating conditions associated with the plurality of sites;
    establishing a ranking order for the plurality of groups;
    iteratively shifting among the sites belong to a highest ranking group till the operating conditions associated with the sites belong to the highest ranking group is substantially identical to the operating conditions associated with the sites belong to a next highest ranking group;
    merging the sites belong to the highest ranking group and the sites belong to the next highest ranking group; and
    iteratively shifting among the sites belong to the merged group.

8. The method of claim 7, further comprising:
    recursively merging with the rest of the plurality of groups until all groups are merged into a single group.

9. A method for laser crystal degradation compensation, comprising:
    defining a plurality of sites on a frequency converting crystal;
    determining an initial operating condition associated with each of the plurality of sites;
    establishing a ranking order based on the initial operating condition associated with each of the plurality of sites;
    determining a degradation rate associated with each of the plurality of sites;
    determining an amount of time T wherein a site is continuously operable within a tolerated variation of at least one beam parameter, the amount of time T being determined based on the tolerated variation of the at least one beam parameter and the degradation rate;
    determining an amount of time t wherein t is a fraction of T; and
    iteratively shifting among the plurality of sites according to the established ranking order, wherein each of the plurality of sites is utilized continuously for a duration of time t for each iteration.

10. The method of claim 9, wherein T represents the amount of time a site is continuously operable without prompting a required optimization to compensate for degradation.

11. The method of claim 9, wherein the same degradation rate is utilized for each of the plurality of sites.

12. The method of claim 11, wherein the degradation rate is pre-determined based on observation of at least one substantially identical crystal.

13. The method of claim 9, wherein the ranking order is established based on the initial operating condition associated with each of the plurality of sites in one of: a descending order or an ascending order.

14. The method of claim 9, further comprising:
    establishing a plurality of groups based on the initial operating conditions associated with the plurality of sites;
    establishing a ranking order for the plurality of groups;
    iteratively shifting among the sites belong to a highest ranking group till the operating conditions associated with the sites belong to the highest ranking group is substantially identical to the operating conditions associated with the sites belong to a next highest ranking group;
    merging the sites belong to the highest ranking group and the sites belong to the next highest ranking group; and
    iteratively shifting among the sites belong to the merged group.

15. The method of claim 14, further comprising:
    recursively merging with the rest of the plurality of groups until all groups are merged into a single group.

16. An illumination apparatus, comprising:
    a laser source; and
    a crystal configured for receiving a laser from the laser source and providing a frequency converted beam as output, the crystal including a plurality of sites defined thereof, wherein each particular site of the plurality of sites is associated with: a degradation rate, and an amount of time T wherein that particular site is continuously operable within a tolerated variation of at least one beam parameter, and wherein the crystal is iteratively shifted among the plurality of sites such that each of the plurality of sites is utilized continuously for a duration of time t for each iteration wherein t is a fraction of T.

17. The illumination apparatus of claim 16, wherein the same degradation rate and the same value of T are utilized for each of the plurality of sites.

18. The illumination apparatus of claim 16, wherein an initial operating condition associated with each of the plurality of sites is determined and a ranking order is established for iteratively shifting among the plurality of sites.

19. The illumination apparatus of claim 16, wherein an initial operating condition associated with each of the plurality of sites is determined, the plurality of sites is divided into multiple groups based on the initial operating conditions associated with each of the plurality of sites, and a ranking order is established for:
- iteratively shifting among the sites belong to a highest ranking group till the operating conditions associated with the sites belong to the highest ranking group is substantially identical to the operating conditions associated with the sites belong to a next highest ranking group;
- merging the sites belong to the highest ranking group and the sites belong to the next highest ranking group; and
- iteratively shifting among the sites belong to the merged group.

20. The illumination apparatus of claim 19, wherein the groups are recursively merged until all groups are merged together into a single group.

\* \* \* \* \*